United States Patent

Kawamura et al.

[11] Patent Number: 5,292,715
[45] Date of Patent: * Mar. 8, 1994

[54] IMINOTHIAZOLINES, THEIR PRODUCTION AND USE AS HERBICIDES

[75] Inventors: Shinichi Kawamura, Osaka; Keiichi Izumi, Nishinomiya; Junichi Sato, Toyonaka; Yuzuru Sanemitsu, Ashiya, all of Japan; Ryo Sato, Durham, N.C.; Tatsuhiro Hamada, Kakogawa; Hideyuki Shibata, Toyonaka, both of Japan

[73] Assignee: Sumitomo Chemical Company, Limited, Osaka, Japan

[*] Notice: The portion of the term of this patent subsequent to Feb. 14, 2010 has been disclaimed.

[21] Appl. No.: 936,516

[22] Filed: Aug. 28, 1992

[30] Foreign Application Priority Data

Aug. 28, 1991 [JP] Japan ................. 3-217175

[51] Int. Cl.$^5$ ............... N01N 43/78; C07D 277/18
[52] U.S. Cl. .................. 504/266; 548/195; 548/196
[58] Field of Search ............. 548/195, 196; 504/266

[56] References Cited

U.S. PATENT DOCUMENTS

| 4,103,017 | 7/1978 | Davies et al. ............ 548/195 |
| 4,867,780 | 9/1989 | Woolard ................... 71/90 |
| 4,913,722 | 4/1990 | Felix et al. .............. 548/195 |

FOREIGN PATENT DOCUMENTS

| 300906 | 7/1988 | European Pat. Off. . |
| 349282 | 6/1989 | European Pat. Off. . |
| 349283 | 6/1989 | European Pat. Off. . |
| 384244 | 2/1990 | European Pat. Off. . |
| 0446802A1 | 3/1991 | European Pat. Off. . |
| 432600A | 6/1991 | European Pat. Off. . |
| 941288 | 3/1956 | Fed. Rep. of Germany . |

Primary Examiner—Robert Gerstl
Attorney, Agent, or Firm—Birch, Stewart, Kolasch & Birch

[57] ABSTRACT

There is disclosed an iminothiazoline compound of the formula:

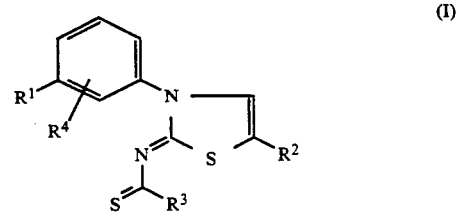

(I)

wherein $R^1$ is halogen, halo(lower)alkyl, halo(lower)alkoxy or halo(lower)alkylthio; $R^2$ is methyl, ethyl, chlorine, bromine or iodine; $R^3$ is lower alkyl, lower cycloalkyl, lower alkoxy, lower cycloalkoxy, lower alkylamino, phenylamino or phenyl, all of which are optionally substituted with at least one substituent selected from halogen, lower alkyl, lower alkoxy, halo(lower)alkyl, lower cycloalkyl and lower cycloalkoxy; and $R^4$ is hydrogen or halogen. Also disclosed are a process for producing this compound, a herbicidal composition comprising this compound as an active ingredient, and a method for controlling undesired weeds by use of this compound as a herbicide.

14 Claims, No Drawings

IMINOTHIAZOLINES, THEIR PRODUCTION AND USE AS HERBICIDES

FIELD OF THE INVENTION

The present invention relates to iminothiazolines, their production and use as herbicides. More particularly, it relates to iminothiazoline compounds having strong herbicidal potency.

BACKGROUND OF THE INVENTION

Certain kinds of iminothiazolidine derivatives are known to be useful as an active ingredient of herbicidal compositions (cf., EP-A-0349282). However, they can hardly be said to be satisfactory herbicides.

OBJECTS OF THE INVENTION

The present inventors have intensively studied to seek satisfactory herbicides and found that particular iminothiazoline compounds have strong herbicidal potency and some of them further exhibit noticeable selectivity between crop plants and weeds.

SUMMARY OF THE INVENTION

The present invention provides iminothiazoline compounds of the formula:

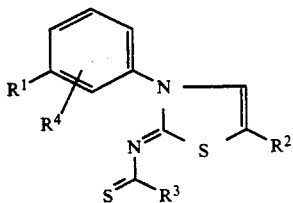

(I)

wherein $R^1$ is halogen, halo(lower)alkyl, halo(lower)alkoxy or halo(lower)alkylthio; $R^2$ is methyl, ethyl, chlorine, bromine or iodine; $R^3$ is lower alkyl, lower cycloalkyl, lower alkoxy, lower cycloalkoxy, lower alkylamino, phenylamino or phenyl, all of which are optionally substituted with at least one substituent selected from halogen, lower alkyl, lower alkoxy, halo(lower)alkyl, lower cycloalkyl and lower cycloalkoxy; and $R^4$ is hydrogen or halogen; more particularly, iminothiazoline compounds of the formula (I), wherein $R^1$ is halogen, halo($C_1$–$C_6$)alkyl, halo($C_1$–$C_6$)alkoxy or halo($C_1$–$C_6$)alkylthio; $R^2$ is methyl, ethyl, chlorine, bromine or iodine; $R^3$ is $C_1$–$C_6$ alkyl, $C_3$–$C_6$ cycloalkyl, $C_1$–$C_6$ alkoxy, $C_3$–$C_6$ cycloalkoxy, $C_1$–$C_6$ alkylamino, phenylamino or phenyl, all of which are optionally substituted with at least one substituent selected from halogen, $C_1$–$C_3$ alkyl, $C_1$–$C_3$ alkoxy, halo($C_1$–$C_3$)alkyl, $C_3$–$C_6$ cycloalkyl and $C_3$–$C_6$ cycloalkoxy; and $R^4$ is hydrogen or halogen.

There is also provided a process for producing the iminothiazoline compounds, which comprises reacting a compound of the formula:

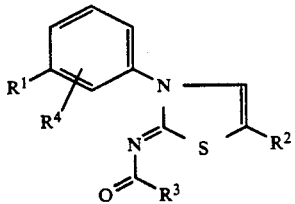

(II)

wherein $R^1$, $R_2$, $R^3$ and $R^4$ are each as defined above with a thio-compound forming agent; or reacting a compound of the formula:

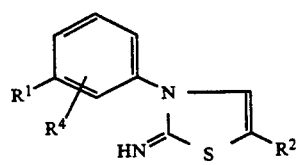

(III)

wherein $R^1$, $R^2$ and $R^4$ are each as defined above with a compound of the formula:

(IV)

wherein $R^3$ is as defined above; or when $R^3$ is alkylamino or phenylamino, reacting a compound of the formula (III) as described above with a compound of the formula:

$$R^5\text{—NCS}\qquad\text{(V)}$$

wherein $R_5$ is alkyl or phenyl, both of which are optionally substituted with at least one substituent selected from halogen, $C_1$–$C_3$ alkyl and $C_1$–$C_3$ alkoxy.

Further provided is a herbicidal composition comprising as an active ingredient the above iminothiazoline compounds (I).

DETAILED DESCRIPTION OF THE INVENTION

The iminothiazoline compounds (I) produce generally strong herbicidal activity against a wide variety of weeds including broad-leaved weeds and Graminaceous weeds in agricultural plowed fields by foliar or soil treatment without producing any material phytotoxicity to crop plants. Examples of the broad-leaved weeds include common purslane (*Portulaca Oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus*

*annuus*), scentless chamomile (*Matricaria perforata*) and corn marigold (*Chrysanthemum segetum*). Examples of Graminaceous weeds include Japanese millet (*Echinochloa frumentacea*), barnyardgrass (*Echinochloa crusqalli*), green foxtail (*Setaria viridis*), yellow foxtail (*Setaria glauca*), southern crabgrass (*Digitaria ciliaris*), large crabgrass (*Digitaria sangui-nalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), giant foxtail (*Setaria faberi*), fall panicum (*Panicum dichotomiflorum*), shattercane (*Sorghum bicolor*) and bermudagrass (*Cynodon dactylon*). Some of the iminothiazoline compounds (I) have the advantage of showing no material chemical injury to various agricultural crops such as corn, wheat, barley, rice plant, soybean, cotton and sugar beet.

The iminothiazoline compounds (I) are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*), waterwort (*Elatine triandra*) and Ammannia multiflora, Cyperaceous weeds such as umbrella sedge (*Cyperus difformis*), hardstem bulrush (*Scirpus juncoides*), needle spikerush (*Eleocharis acicularis*) and water nutgrass (*Cyperus serotinus*), and others such as monochoria (*Monochoria vaginalis*) and arrowhead (*Sagittaria pygmaea*). Some of the iminothiazoline compounds (I) have the advantage of showing no phytotoxicity to rice plants on flooding treatment.

As used herein, the term "$C_n$-$C_m$" refers to the carbon number of a group immediately following this term. In case of $C_1$-$C_6$ alkylcarbonyl, for instance, the term "$C_1$-$C_6$" indicates the carbon number of its alkyl portion and exclude that of its carbonyl portion Also, a group substituted with a substituent preferably covers a group bearing from 1 to 10 substituents which may be the same or different.

Among the iminothiazoline compounds (I), preferred are those wherein $R^1$ is halo($C_1$-$C_3$)alkyl, more preferably trifluoromethyl; those wherein $R^2$ is methyl or ethyl; those wherein $R^3$ is $C_1$-$C_6$ alkyl or $C_3$-$C_6$ cycloalkyl, both of which are optionally substituted with at least one substituent selected from halogen, $C_1$-$C_3$ alkyl and $C_1$-$C_3$ alkoxy; and those wherein $R^4$ is hydrogen or fluorine at the para position. Typical examples of the most preferred compounds are as follows:

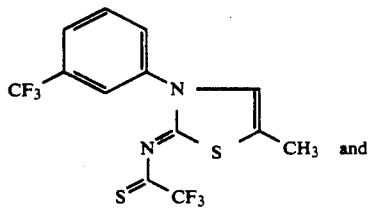

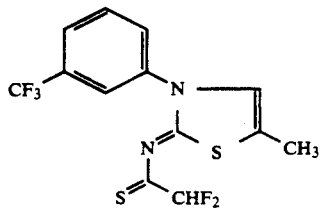

Procedures for producing the iminothiazoline compounds (I) of the present invention will hereinafter be explained in detail.

The iminothiazoline compounds (I) can be produced by reacting iminothiazoline compounds (II) of the formula:

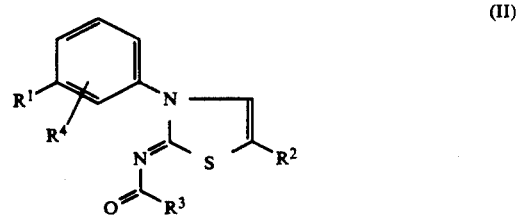

(II)

wherein $R^1$, $R^2$, $R^3$ and $R^4$ are each as defined above with a thio-compound forming agent.

This reaction is usually carried out in a solvent at a temperature of about 20° to 200° C. for a period of 2 to 200 hours. The thio-compound forming agent is used at a proportion of 1 to 10 equivalents to one equivalent of the compound (II). As the solvent, there may be exemplified, aromatic hydrocarbons (e.g., benzene, toluene, xylene) and ethers (e.g., diethyl-ether, diisopropyl ether, dioxane, tetrahydrofuran, diethylene glycol dimethyl ether). These solvents may be used solely or in combination. Examples of the thio-compound forming agent are those of the inorganic type (e.g., phosphorus pentasulfide) and those of the organic type (e.g., Lawesson agent, Davy agent).

Also, the iminothiazoline compounds (I) can also be obtained, according to the method as described in EP-A-0446802, by reacting iminothiazoline derivatives of the formula:

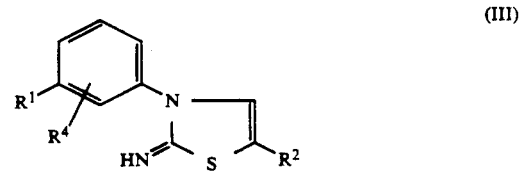

(III)

wherein $R^1$, $R^2$ and $R^4$ are each as defined above, with an acid chloride of the formula:

(IV)

wherein $R^3$ is as defined above.

In cases where $R^3$ is alkylamino or phenylamino, the iminothiazoline compounds (I) can be obtained by reacting the iminothiazoline derivatives of the formula (III) with an isothiocyanate derivative of the formula:

$R^5$—NCS   (V)

wherein $R^5$ is alkyl or phenyl, both of which are optionally substituted with at least one substituent selected from halogen, $C_1$-$C_3$ alkyl and $C_1$-$C_3$ alkoxy.

After completion of the reaction, the reaction mixture may be subjected to ordinary post-treatment in a conventional manner such as extraction with an organic solvent and concentration. If necessary, any purification method (e.g., chromatography, recrystallization)

may be further utilized to give the objective compound (I).

Typical examples of the iminothiazoline compounds (I) produced by the above procedure are shown in Table 1.

TABLE 1

(I)

| R¹ | R² | R³ | R⁴ |
|---|---|---|---|
| CF₃ | CH₃ | C(CH₃)₃ | H |
| CF₃ | C₂H₅ | 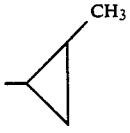 | H |
| CF₃ | CH₃ | CF₃ | H |
| CF₃ | CH₃ | CF₃ | 4-F |
| CF₃ | C₂H₅ | CF₃ | 4-F |
| CF₃ | C₂H₅ | CF₃ | H |
| CF₃O | CH₃ | n-C₄H₉ | H |
| Cl | Cl | n-C₃H₇ | 5-F |
| Br | Br | n-C₄H₉ | H |
| CF₃ | I | CF₃ | 2-F |
| CF₃ | CH₃ |  | 4-Cl |
| CF₃S | C₂H₅ | C₂H₅ | H |
| CF₃S | CH₃ | 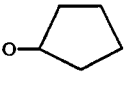 | 4-F |
| CHF₂O | CH₃ | 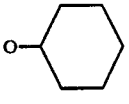 | H |
| CF₃ | CH₃ |  | H |
| Cl | Br | O-n-C₆H₁₃ | H |
| Br | CH₃ | O-i-C₃H₇ | 4-Cl |
| CF₃ | CH₃ | O-n-C₄H₉ | H |
| CF₃ | CH₃ | NHCH₃ | H |
| CF₃ | CH₃ | NH-i-C₃H₇ | 2-F |
| CF₃O | CH₃ | CF₃ | H |
| CF₃ | C₂H₅ | 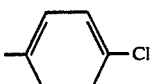 | H |
| CF₃ | CH₃ | 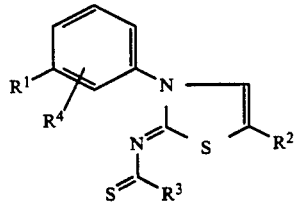 | H |

TABLE 1-continued

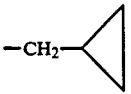

(I)

| R¹ | R² | R³ | R⁴ |
|---|---|---|---|
| CF₃ | CH₃ | 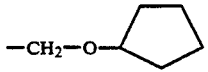 | H |
| CF₃ | C₂H₅ | 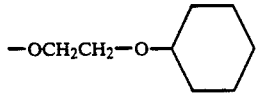 | 4-F |
| CF₃ | CH₃ | 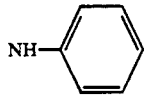 | H |
| CF₃ | CH₃ | n-C₆H₁₃ | H |
| CF₃ | CH₃ | 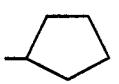 | H |
| C₂F₅ | CH₃ | n-C₃H₇ | H |
| CF₂HCF₂O | CH₃ | C₂H₅ | H |
| CF₃ | CH₃ | 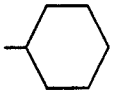 | H |
| CF₃ | CH₃ | 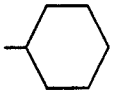 | H |

It should be noted that the iminothiazoline compounds (I) include their stereo isomers having herbicidal activity.

The iminothiazoline compounds (II) and (III) may be produced by the method as described in EP-A-0446802.

For the practical usage of the iminothiazoline compounds (I), they are usually formulated with conventional solid or liquid carriers or diluents as well as surface active agents, or other auxiliary agents into conventional formulations such as emulsifiable concentrates, wettable powders, flowables, granules and water-dispersible granules.

These formulations contain the iminothiazoline compounds (I) as an active ingredient at a content within the range of about 0.02% to 90% by weight, preferably of about 0.05% to 80% by weight.

Examples of the solid carrier or diluent are fine powders or granules of kaolin clay, attapulgite clay, terra alba, pyrophyllite, talc, diatomaceous earth, calcite, walnut shell powders, urea, ammonium sulfate and synthetic hydrous silica. As the liquid carrier or diluent, there may be exemplified aromatic hydrocarbons (e.g., xylene, methyl-naphthalene), alcohols (e.g., isopropanol, ethylene glycol, cellosolve), ketones (e.g., acetone, cyclohexanone, isophorone), vegetable oils (e.g., soybean oil, cotton seed oil), dimethylsulfoxide, N,N-dimethylformamide, acetonitrile and water.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters and polyoxyethylene sorbitan fatty acid esters. Examples of the auxiliary agent include ligninsulfonates, sodium alginate, polyvinyl alcohol, gum arabic, CMC (carboxymethyl cellulose) and PAP (isopropyl acid phosphate).

The iminothiazoline compounds (I) are usually formulated in any suitable formulation and used for pre-emergence or post-emergence control of undesired weeds by soil treatment, foliar treatment or flood fallowing treatment. These treatments include application to the soil surface prior to or after planting, incorporation into the soil prior to planting or transplanting, and the like. The foliar treatment may be effected by spraying a herbicidal composition containing the iminothiazoline compounds (I) over the top of plants. It may also be applied directly to the weeds if care must be taken to keep the chemical off the crop foliage.

The dosage of the iminothiazoline compounds (I) may vary depending on the prevailing weather conditions, formulation used, prevailing season, mode of application, soil involved, crop and weed species, and the like. Usually, however, the dosage is from about 10 to 5000 grams, preferably from about 20 to 2000 grams, of the active ingredient per hectare. The herbicidal composition thus formulated in the form of an emulsifiable concentrate, wettable powder or flowable may usually be employed by diluting it with water at a volume of about 100 to 1000 liters per hectare, if necessary, with addition of an auxiliary agent such as a spreading agent. The herbicidal composition formulated in the form of granules may usually be applied as such without dilution.

Examples of the spreading agent include, in addition to the surface active agents as described above, polyoxyethylene resin acid (ester), ligninsulfonate, abietylenic acid salt, dinaphthylmethanedisulfonate and paraffin.

The iminothiazoline compounds (I) are useful as a herbicide to be employed for paddy filed, crop field, orchards, pasture land, lawns, forests and non-agricultural fields. Further, the iminothiazoline compounds (I) may also be used together with any other herbicide to improve their herbicidal activity, and in some cases, synergistic effects can be expected. Furthermore, these compounds may be applied in combination with insecticides, acaricides, nematocides, fungicides, plant growth regulators, fertilizers, soil improvers and the like.

The present invention will be explained in more detail by way of Preparation Examples, Reference Examples, Formulation Examples and Test Examples, to which however the invention is not limited in any way.

Practical and presently preferred embodiments for production of the iminothiazoline compounds (I) are illustrated in the following examples.

PREPARATION EXAMPLE 1

A solution of 2-[(t-butylcarbonyl)imino]-3-[3-(trifluoromethyl)phenyl]-5-methylthiazoline (1 g) and 2,4bis(4-methoxyphenyl)-1,3-dithia-2,4-diphosphetane-2,4disulfide (2 g) in THF (10 ml) was refluxed for 2 days. After cooling and removal of the solvent under reduced pressure, the concentrated residue was added pottasium hydrogencarbonate. The obtained crystallines were recrystallized to give 0.6 g of 2-[t-butyl(thiocarbonyl)]imino-3-[3-(trifluoromethyl)phenyl]-5-methylthiazoline (Compound No. 3).

PREPARATION EXAMPLE 2

A solution of 2-(trifluoroacetyl)imino-3-[3-(trifluoromethyl)phenyl]-5-methylthiazoline (1 g) and 2,4-bis(4-methoxyphenyl)-1,3-dithia-2,4-diphosphetane-2,4-disulfide (2 g) in THF (10 ml) was refluxed for 2 days. After cooling and removal of the solvent under reduced pressure, the concentrated residue was added pottasium hydrogencarbonate, The obtained crystallines were recrystallized to give 0.5 g of 2-[trifluoromethyl(thiocarbonyl)imino]-3-[3-(trifluoromethyl)phenyl]-5-methylthiazoline (Compound No. 2)

PREPARATION EXAMPLES 3 and 4

In the same manner as above, the iminothiazoline compounds (I) as shown in Table 2 were obtained.

TABLE 2

(I)

| Compound No. | $R^1$ | $R^2$ | $R^3$ | $R^4$ | m.p. (°C.) |
|---|---|---|---|---|---|
| 1 | $CF_3$ | $C_2H_5$ | cyclopropyl | H | 101.8 |
| 2 | $CF_3$ | $CH_3$ | $CF_3$ | H | 151.2 |
| 3 | $CF_3$ | $CH_3$ | $C(CH_3)_3$ | H | 97.8 |
| 4 | $CF_3$ | $CH_3$ | 2-F-phenyl-NH | H | 147.6 |
| 5 | $CF_3$ | $C_2H_5$ | methylcyclopropyl | H | 116.0 |
| 6 | $CF_3$ | $CH_3$ | $CH_3$ | 4-Cl | 193.7 |
| 7 | $CF_3$ | $C_2H_5$ | $CH_3$ | H | 141.9 |
| 8 | $CF_3$ | Br | $CH_3$ | H | 159.2 |
| 9 | $OCHF_2$ | $CH_3$ | $CHF_2$ | H | 106.2 |

TABLE 2-continued

Structure (I):

Phenyl ring with substituents $R^1$, $R^4$ attached to N, connected to C=N with S, and C=S-$R^3$, with substituent $R^2$ on the vinyl group.

| Compound No. | $R^1$ | $R^2$ | $R^3$ | $R^4$ | m.p. (°C.) |
|---|---|---|---|---|---|
| 10 | CF$_3$ | CH$_3$ | NH—(2-Cl-phenyl) | H | 112.7 |
| 11 | CF$_3$ | CH$_3$ | NH—(4-Cl-phenyl) | H | 214.0 |
| 12 | CF$_3$ | CH$_3$ | NH—(3-CF$_3$-phenyl) | H | 191.3 |
| 13 | CF$_3$ | CH$_3$ | CH$_3$ | H | 161.6 |
| 14 | CF$_3$ | CH$_3$ | CH$_3$ | 4-F | 130.0 |
| 15 | CF$_3$ | CH$_3$ | CHF$_2$ | H | 115.0 |
| 16 | CF$_3$ | C$_2$H$_5$ | CH$_2$OCH$_3$ | H | 137.7 |
| 17 | CF$_3$ | CH$_3$ | CH$_2$CH$_2$CH$_3$ | H | 127.7 |

The following illustrates practical embodiments of the herbicidal composition according to the present invention wherein parts are by weight. The compound number of the active ingredient corresponds to that of Table 2.

FORMULATION EXAMPLE 1

Fifty parts of any one of Compound Nos. 1 to 17, 3 parts of calcium ligninsulfonate, 2 parts of sodium laurylsulfate and 45 parts of synthetic hydrous silica are well mixed while being powdered to obtain wettable powder.

FORMULATION EXAMPLE 2

Five parts of any one of Compound Nos. 1 to 17, 15 parts of "Toxanone P8L$^R$" (commercially available surface active agent; Sanyo Kasei K.K.) and 80 parts of cyclohexanone are well mixed to obtain emulsifiable concentrate.

FORMULATION EXAMPLE 3

Two parts of any one of Compound Nos. 1 to 17, 1 part of synthetic hydrous silica, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of any one of Compound Nos. 1 to 17 are mixed with 3 parts of polyoxyethylene sorbitan monooleate, 3 parts of carboxymethyl cellulose (CMC) and 69 parts of water and pulverized until the particle size of the mixture becomes less than 5 microns to obtain a suspension.

The biological data of the iminothiazoline compound (I) as the herbicide will be illustrated in the following Test Examples wherein the phytotoxicity to crop plants and the herbicidal activity on weeds were determined by visual observation as to the degree of germination as well as the growth inhibition and rated with an index 0, 1, 2, 3, 4, 5, 6, 7, 8, 9 or 10, the numeral "0" indicating no material difference as seen in comparison with the untreated plants and the numeral "10" indicating the complete inhibition or death of the test plants. The compound number in the biological data corresponds to that shown in Table 2.

The compounds as shown in Table 3 were used for comparison.

TABLE 3

| Compound No. | Structure | Remarks |
|---|---|---|
| A | Cl—phenyl—CH$_2$SC(=O)—N(C$_2$H$_5$)$_2$ | Benthiocarb (commercially available herbicide) |
| B | 3-F-phenyl-N attached to thiazoline ring with N=C—OC$_2$H$_5$(=O) | EP-A-0349282 |
| C | 3-EtO-phenyl-N attached to thiazoline ring with N=C—OC$_2$H$_5$(=O) | EP-A-0349282 |

TEST EXAMPLE 1

Cylindrical plastic pots (diameter, 10 cm; height, 10 cm) were filled with upland field soil, and the seeds of japanese millet, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a greenhouse for 20 days, and the herbicidal activity was examined. The results are shown in Table 4.

TABLE 4

| Compound No. | Dosage (g/ha) | Herbicidal activity | | |
|---|---|---|---|---|
| | | Japanese millet | Tall morningglory | Velvetleaf |
| 1 | 2000 | 10 | 10 | 9 |
|   | 500 | 9 | 10 | 8 |
| 2 | 2000 | 9 | 10 | 10 |
|   | 500 | 9 | 7 | 7 |
| 9 | 500 | 9 | 10 | 10 |

TABLE 4-continued

| Compound No. | Dosage (g/ha) | Herbicidal activity | | |
|---|---|---|---|---|
| | | Japanese millet | Tall morning-glory | Velvet-leaf |
| 15 | 500 | 10 | 9 | 10 |
| | 125 | 8 | 7 | 7 |
| A | 2000 | 7 | 0 | 0 |
| | 500 | 0 | 0 | 0 |
| B | 2000 | 0 | 0 | 0 |
| C | 2000 | 0 | 0 | 0 |
| | 500 | 0 | 0 | 0 |

TEST EXAMPLE 2

Cylindrical plastic pots (diameter, 10 cm; height, 10 cm) were filled with upland filed soil, and the seeds of japanese millet, morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 1000 liters per hectare. The test plants were further grown in the greenhouse for 20 days, and the herbicidal activity was examined. The results are shown in Table 5.

TABLE 5

| Compound No. | Dosage (g/ha) | Herbicidal activity | | | |
|---|---|---|---|---|---|
| | | Japanese millet | Morning-glory | Radish | Velvet-leaf |
| 1 | 2000 | 9 | 10 | 10 | 10 |
| | 500 | 9 | 10 | 10 | 10 |
| | 125 | 9 | 9 | 9 | 7 |
| 2 | 2000 | 9 | 10 | 10 | 10 |
| | 500 | 9 | 10 | 10 | 10 |
| 3 | 2000 | 9 | 9 | 9 | 9 |
| | 500 | 9 | 9 | 9 | 9 |
| 4 | 2000 | 7 | 9 | 8 | 9 |
| 5 | 500 | 10 | 10 | 8 | 7 |
| 9 | 500 | 10 | 8 | 10 | 7 |
| 15 | 500 | 10 | 10 | 10 | 9 |
| | 125 | 9 | 9 | 10 | 7 |
| 16 | 500 | 10 | 9 | 10 | 8 |
| | 125 | 10 | 9 | 9 | 7 |
| A | 2000 | 9 | 2 | 1 | 0 |
| | 500 | 3 | 1 | 0 | 0 |
| B | 2000 | 1 | 3 | 0 | 0 |
| | 500 | 0 | 1 | 0 | 0 |
| C | 2000 | 0 | 2 | 1 | 0 |
| | 500 | 0 | 1 | 0 | 0 |

TEST EXAMPLE 3

Cylindrical plastic pots (diameter, 8 cm; height, 12 cm) were filled with paddy field soil, and the seeds of barnyardgrass (Echinochloa oryzicola) were sowed in 1 to 2 cm depth. Water was poured therein to make a flooded condition, and rice seedlings of 2-leaf stage were transplanted therein, and the test plants were grown in a greenhouse. After six days (at that time seeds began to germinate), a designated amount of the test compound formulated in an emulsifiable concentrate as in Formulation Example 2 and diluted with water (2.5 ml) was applied to the pots by perfusion. The test plants were grown for additional 19 days in the greenhouse, and the herbicidal activity and phytotoxicity were examined. The results are shown in Table 6.

TABLE 6

| Compound No. | Dosage (g/ha) | Phyto-toxicity Rice plant | Herbicidal activity Barnyard-grass |
|---|---|---|---|
| 1 | 63 | 0 | 8 |
| 2 | 63 | 0 | 7 |
| 4 | 63 | 0 | 8 |
| 5 | 63 | 0 | 7 |
| 6 | 63 | 0 | 7 |
| 7 | 63 | 1 | 10 |
| 8 | 250 | 1 | 10 |
| 9 | 250 | 0 | 7 |
| 10 | 250 | 1 | 8 |
| 13 | 63 | 1 | 7 |
| 14 | 63 | 1 | 9 |
| 15 | 250 | 1 | 8 |
| 16 | 250 | 2 | 10 |
| 17 | 63 | 2 | 9 |
| | 16 | 0 | 7 |
| A | 63 | 0 | 2 |
| B | 250 | 0 | 0 |
| C | 250 | 0 | 0 |

TEST EXAMPLE 4

Vats (33 cm × 23 cm × 11 cm) were filled with upland field soil, and the seeds of cotton, black nightshade and green foxtail were sowed in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 1000 liters per hectare. The test plants were grown in a greenhouse for 20 days, and the herbicidal activity and phytotoxicity were examined. The results are shown in Table 7.

TABLE 7

| Compound No. | Dosage (g/ha) | Phyto-toxicity Cotton | Herbicidal activity | |
|---|---|---|---|---|
| | | | Black nightshade | Giant foxtail |
| 1 | 500 | 0 | 10 | 10 |
| 2 | 125 | 0 | 8 | 10 |
| 7 | 500 | 0 | 9 | 7 |
| 8 | 500 | 0 | 7 | — |
| 9 | 250 | 0 | 9 | 7 |
| 13 | 500 | 0 | 10 | 9 |
| 14 | 500 | 0 | 10 | 10 |
| 15 | 500 | 0 | 10 | 10 |
| 16 | 500 | 0 | 10 | 10 |
| 17 | 500 | 0 | 10 | 10 |
| A | 500 | 0 | 0 | 6 |
| B | 500 | 0 | 0 | 0 |
| C | 500 | 0 | 0 | 0 |

TEST EXAMPLE 5

Vats 33 cm × 23 cm × 11 cm) were filled with upland field soil, and the seeds of persian speedwell and wheat were sowed in 1 to 2 cm depth. A designated amount of the test compound formulated in an emulsifiable concentrate as in Formulation Example 2 was diluted with water, and the dilution was sprayed onto the soil surface by means of an automatic sprayer at a spray volume of 1000 liters per hectare. The test plants were grown in a greenhouse for 25 days, and the herbicidal activity and phytotoxicity were examined. The results are shown in Table 8.

TABLE 8

| Compound No. | Dosage (g/ha) | Phytotoxicity Wheat | Herbicidal activity Persian speedwell |
|---|---|---|---|
| 1 | 32 | 0 | 10 |
| 2 | 125 | 1 | 8 |
| 7 | 32 | 0 | 9 |
| 13 | 32 | 0 | 10 |
| 14 | 32 | 0 | 10 |
| 15 | 32 | 1 | 10 |
| 17 | 32 | 0 | 10 |
| B | 250 | 0 | 0 |
| C | 250 | 0 | 0 |

TEST EXAMPLE 6

Wagner's pots (1/5000 are) were filled with paddy field soil, and the seeds of barnyardgrass and monochoria (*Monochoria vaginalis*) were sowed in 1 to 2 cm depth. Water was poured therein to make a flooded condition, and rice seedling of 3-leaf stage were transplanted therein, and the test plants were grown in a greenhouse. After five days (at that time barnyardgrass began to germinate), a designated amount of the test compound formulated in an emulsifiable concentrate as in Formulation Example 2 and diluted with water (10 ml) was applied to the pots by perfusion. The test plants were grown for additional 19 days in the greenhouse, and the herbicidal activity and phytotoxicity were examined. The results are shown in Table 9. At the time of the treatment, the depth of water in the pots was kept at 4 cm, and for the following two days, water was allowed to leak at a volume corresponding to the depth of 3 cm per day.

TABLE 9

| Compound No. | Dosage (g/ha) | Phytotoxicity Rice plant | Herbicidal activity Barnyardgrass | Herbicidal activity Monochoria |
|---|---|---|---|---|
| 1 | 63 | 0 | 8 | 10 |
| 2 | 63 | 0 | 7 | 10 |
| 4 | 63 | 0 | 8 | 10 |
| 5 | 63 | 0 | 7 | 10 |
| 10 | 250 | 1 | 8 | 10 |
| 14 | 63 | 1 | 9 | 10 |
| 17 | 63 | 2 | 9 | 10 |
| A | 250 | 0 | 7 | 0 |
|   | 63 | 0 | 0 | 0 |
| B | 250 | 0 | 0 | 0 |
| C | 250 | 0 | 0 | 0 |

What is claimed is:

1. An iminothiazoline compound of the formula:

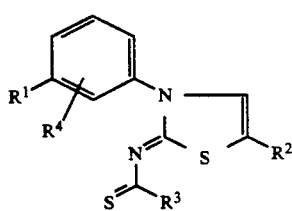

(I)

wherein $R^1$ is halogen, halo(lower)alkyl, halo(lower)alkoxy or halo(lower)alkylthio; $R^2$ is methyl, ethyl, chlorine, bromine or iodine; $R^3$ is lower alkyl, lower cycloalkyl, lower alkoxy, lower cycloalkoxy, lower alkylamino, phenylamino or phenyl, all of which are optionally substituted with at least one substituent selected from halogen, lower alkyl, lower alkoxy, halo(lower)alkyl, lower cycloalkyl and lower cycloalkoxy; and $R^4$ is hydrogen or halogen.

2. An iminothiazoline compound of the formula:

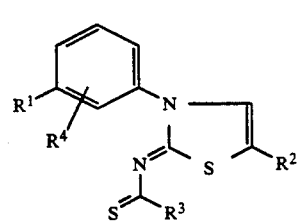

(I)

wherein $R^1$ is halogen, halo($C_1$-$C_6$)alkyl, halo($C_1$-$C_6$)alkoxy or halo($C_1$-$C_6$)alkylthio; $R^2$ is methyl, ethyl, chlorine, bromine or iodine; $R^3$ is $C_1$-$C_6$ alkyl, $C_3$-$C_6$ cycloalkyl, $C_1$-$C_6$ alkoxy, $C_3$-$C_6$ cycloalkoxy, $C_1$-$C_6$ alkylamino, phenylamino or phenyl, all of which are optionally substituted with at least one substituent selected from halogen, $C_1$-$C_3$ alkyl, $C_1$-$C_3$ alkoxy, halo($C_1$-$C_3$)alkyl, $C_3$-$C_6$ cycloalkyl and $C_3$-$C_6$ cycloalkoxy; and $R^4$ is hydrogen or halogen.

3. A compound according to claim 2, wherein $R^2$ is methyl or ethyl.

4. A compound according to claim 2, wherein $R^1$ is halo($C_1$-$C_3$)alkyl.

5. A compound according to claim 2, wherein $R^3$ is $C_1$-$C_6$ alkyl or $C_3$-$C_6$ cycloalkyl, both of which are optionally substituted with at least one substituent selected from halogen, $C_1$-$C_3$ alkyl and $C_1$-$C_3$ alkoxy.

6. A compound according to claim 2, wherein $R^4$ is hydrogen or fluorine at the 4-position.

7. A compound according to claim 5, wherein $R^2$ is methyl or ethyl.

8. A compound according to claim 5, wherein $R^1$ is halo($C_1$-$C_3$)alkyl.

9. A compound according to claim 5, wherein $R^4$ is hydrogen or fluorine at the 4-position.

10. A compound according to claim 8, wherein $R^2$ is methyl or ethyl.

11. A compound according to claim 4, wherein $R^1$ is $CF_3$.

12. A compound according to claim 1, which is

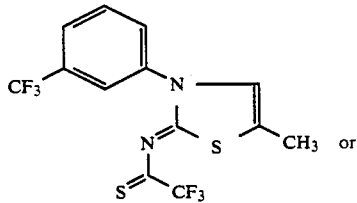

or

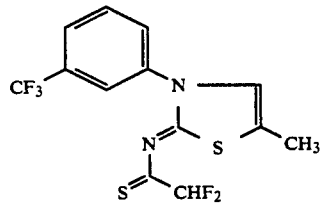

13. A herbicidal composition which comprises as an active ingredient a herbicidally effective amount of the compound according to claim 1, and an inert carrier or diluent.

14. A method for controlling undesired weeds, which comprises applying a herbicidally effective amount of the compound according to claim 1 and an inert carrier or diluent to the area where undesired weeds grow or will grow.

* * * * *

UNITED STATES PATENT AND TRADEMARK OFFICE
CERTIFICATE OF CORRECTION

PATENT NO. : 5,292,715
DATED : 3-8-94
INVENTOR(S) : Shinichi KAWAMURA et al

It is certified that error appears in the above-indentified patent and that said Letters Patent is hereby corrected as shown below:

On the title page,
Changing the information in the "[*] Notice" section describing the disclaimed patent term portion such that the incorrect date of "Feb. 14, 2010" is corrected so as to read --Sept. 14, 2010--.

Signed and Sealed this

Fifth Day of July, 1994

*Attest:*

BRUCE LEHMAN

*Attesting Officer*   Commissioner of Patents and Trademarks